United States Patent [19]

Cavan

[11] Patent Number: 4,659,172

[45] Date of Patent: Apr. 21, 1987

[54] ROTATABLE AND TRANSLATABLE MOUNTING MECHANISM FOR A SPECIMEN PATTERN IN OPTICAL PROCESSING APPARATUS

[75] Inventor: Daniel L. Cavan, Woodside, Calif.

[73] Assignee: Insystems, Inc., San Jose, Calif.

[21] Appl. No.: 736,230

[22] Filed: May 20, 1985

[51] Int. Cl.[4] .......................... G03H 1/02; G03H 1/22
[52] U.S. Cl. ..................................... 350/3.83; 350/3.6; 350/3.85; 350/3.86
[58] Field of Search ................. 350/3.85, 162.12, 3.83, 350/3.86, 3.6

[56] References Cited

U.S. PATENT DOCUMENTS 4,478,481 10/1984 Fusek et al. ........................ 350/3.83

*Primary Examiner*—Bruce Y. Arnold
*Attorney, Agent, or Firm*—Stoel, Rives, Boley, Fraser & Wyse

[57] ABSTRACT

A translatable and rotatable mechanism is employed in optical processing apparatus for exposing a specimen pattern and inspecting light pattern or image developed from it. The mounting mechanism includes a plate that is rotatably mounted on a linear positioning table assembly. The plate includes a substrate arm and a camera arm that extend in opposite directions from the axis of rotation of the plate. The specimen pattern, such as a photomask, is positioned on the free end of the substrate arm, and a video camera is positioned on the free end of the camera arm. Whenever the plate is rotated to an exposure orientation, the photomask diffracts light rays emanating from a laser. The diffracted light rays interfere with a reference beam to form a hologram. Whenever the plate is rotated 180° to an inspection orientation, a reconstructed imate of the photomask appears at the location where the photomask was positioned during exposure. The video camera is positioned directly beneath the reconstructed image and scans it by the translational movement of the positioning table. A microscope is mounted to a stationary support and is positioned over the photomask. The video camera and the microscope observe corresponding regions of the image and the photomask, respectively, in synchronism for all translational movements of the plate.

10 Claims, 5 Drawing Figures

ROTATABLE AND TRANSLATABLE MOUNTING MECHANISM FOR A SPECIMEN PATTERN IN OPTICAL PROCESSING APPARATUS

BACKGROUND OF THE INVENTION

The present invention relates to optical processing apparatus, and in particular, a mechanism that is included in such apparatus for mounting a specimen pattern and providing automatic self-tracking of corresponding regions of the specimen pattern and light pattern or image which is developed from it.

Optical processing apparatus have been used to produce images of specimen subjects for the purpose of examining certain characteristics of them. One such apparatus that employs holographic techniques to develop a three-dimensional image of a subject volume is described in U.S. Pat. No. 4,478,481 of Fusek et al.

In the system of Fusek et al., parallel rays of coherent light strike the subject volume which diffracts them. The diffracted light rays pass through an imaging lens and interfere with a collimated reference beam in a photosensitive recording material to form a hologram of the subject volume. After it is exposed and developed, the recording medium is illuminated by a beam of light that propagates along the path in the conjugate direction of the reference beam to reconstruct from the hologram an image of the subject volume. The light rays reconstructed from the hologram exactly retrace their original paths back through the optical system and provide a three-dimensional real image at the plane of the subject volume. The image produced is then examined by a microscope or other suitable viewing instrument.

Since the reconstructed image appears in the same location where the subject volume was positioned during exposure, it would be advantageous to have a simple mechanism that facilitates not only the exposure of the subject, but also the tracking and inspection of corresponding regions of the reconstructed image and the subject from which the image was developed.

SUMMARY OF THE INVENTION

An object of the present invention is, therefore, to provide in an optical processing apparatus a simple mechanism for mounting a specimen subject to expose and record it and for inspecting an image developed from and corresponding to it.

Another object of this invention is to provide such a mechanism that facilitates automatic tracking and inspection of corresponding regions of the specimen subject and the image.

A further object of this invention is to provide such a mechanism in an apparatus for inspecting an image reconstructed from a hologram.

The present invention is a translatable and rotatable mounting mechanism for a specimen subject, such as, for example, a photomask. The mounting mechanism includes a plate that is rotatably mounted on a linear positioning table assembly, which is operable for travel to selectable X-Y position coordinate combinations. The plate includes a substrate arm and a camera arm that extend in opposite directions from the axis of rotation of the plate. The photomask is positioned on the free end of the substrate arm, and a video camera is positioned on the free end of the camera arm.

Whenever the plate is rotated to the exposure orientation, the photomask receives light rays emanating from a laser and diffracts them. The diffracted light rays propagate through an optical system and interfere with a reference beam to form a hologram.

Whenever the plate is rotated 180° to the inspection orientation, a beam of light propagating in the conjugate direction of the reference beam strikes the hologram. A reconstructed image of the photomask then appears at the location where the photomask was positioned during exposure. The video camera, which is positioned beneath the reconstructed image, scans the image by the movement of the X-Y positioning table, and thereby the movement of the substrate, in a plane that is parallel to that of the image. A microscope is mounted to a stationary support and is positioned over the photomask so that the field of view of the video camera corresponds to that of the microscope. The video camera and the microscope observe, therefore, corresponding regions of the image and the photomask, respectively, in synchronism for all translational movements of the substrate.

Additional objects and advantages of the present invention will be apparent from the following detailed description of a preferred embodiment thereof, which proceeds with reference to the accompanying drawings.

DETAILED DESCRIPTION OF PREFERRED EMBODIMENT

Figure 1:
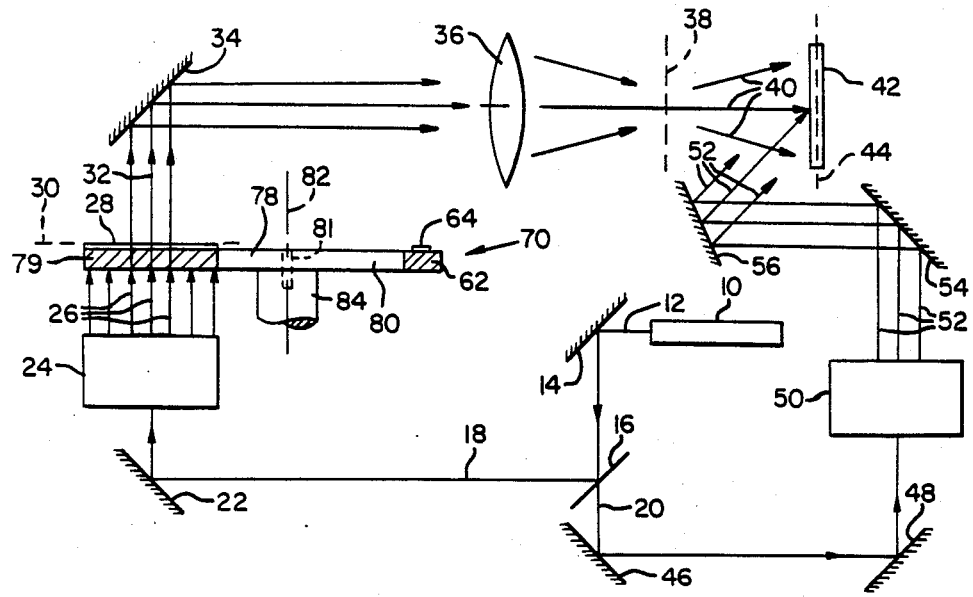
FIG. 1 is a side elevation view of a schematic layout of an optical processing apparatus showing part of the mounting mechanism in the exposure orientation for constructing a hologram of the specimen pattern.

FIG. 1 is a diagram of an optical system for forming a hologram of a specimen pattern.

With reference to FIG. 1, a laser 10 provides a beam of coherent light 12 that reflects off mirror 14 and strikes beam splitter 16, which divides the beam of light 12 into a subject beam component 18 and a reference beam component 20. Subject beam 18 strikes and reflects off mirror 22 and passes through beam expander 24. The parallel coherent light rays 26 exiting beam expander 24 illuminate a photomask 28 of rectangular shape, which lies in a horizontal subject plane 30 and serves as a specimen pattern in the preferred embodiment described herein.

The light rays 32 diffracted by photomask 28 reflect off mirror 34 and strike lens 36 which brings the light rays propagating through it to a focus in a filter plane 38. The light rays 40 passing through filter plane 38 strike a photosensitive recording medium 42 in a hologram plane 44, which is parallel to filter plane 38.

The reference beam 20 exiting beam splitter 16 reflects off and is directed by mirrors 46 and 48 to beam expander 50. The parallel coherent reference beam light rays 52 exiting beam expander 50 reflect off and are directed by mirrors 54 and 56 to interfere with the light rays 40 at hologram plane 44. After completion of the exposure process, recording medium 42 is photographically developed to record in the form of a hologram light information corresponding to photomask 28.

Figure 2:
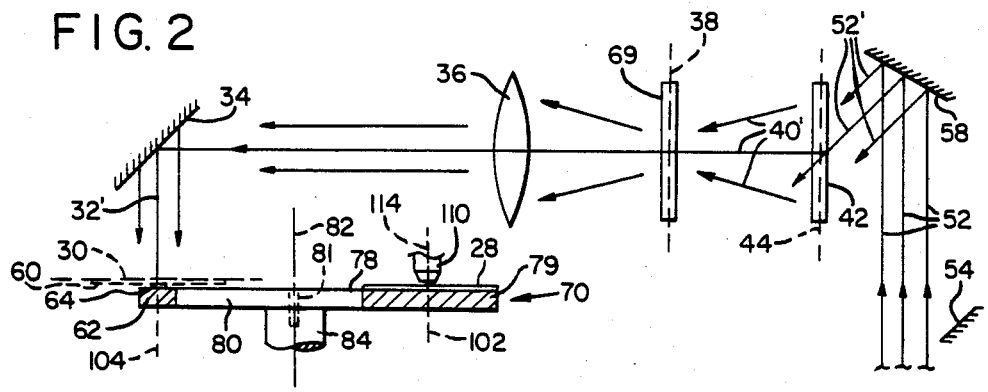
FIG. 2 is a fragmentary schematic layout of the optical processing apparatus of FIG. 1 showing part of the mounting mechanism in the inspection orientation for reconstructing the image from the hologram and inspecting the image.

FIG. 2 shows the optical apparatus for reconstructing the image of photomask 28 from hologram 42. The optical components depicted in FIG. 1 for developing light rays 52 that form the reference beam for the hologram 42 are omitted for purposes of clarity only. In addition, mirror 22 is removed to prevent the transmission of subject beam 18 to subject plane 30 during image reconstruction.

With reference to FIG. 2, mirror 54 is removed from the path of light rays 52 to allow them to strike a mirror 58 which is positioned so that the light rays 52' reflected from it strike hologram 42 along the path in the opposite or conjugate direction of reference beam light rays 52. Light rays 52' strike hologram 42 in the conjugate direction to reconstruct the light information recorded in hologram 42. Reconstructed light rays 40' travel along the same path in the opposite direction to the light rays 40 that originally propagated through lens 36 to form the hologram. The light rays 32' that exit lens 36 reflect off mirror 34 to form at subject plane 30 an image 60 corresponding to the specimen pattern of photomask 28. A detecting means 62, such as a video camera, having an aperture 64 with a predetermined field of view is positioned for movement along the subject plane 30 to detect the presence of light in certain regions of image 60 as will be further described.

In a preferred embodiment, a spatial filter 69 representing the Fourier transform of an error-free photomask is positioned at filter plane 38, which is located one focal length away from lens 36. Positioning the spatial filter 69 in plane 38 in the above-described location develops at subject plane 30 an image 60 that corresponds only to the defects present in photomask 28.

It will be appreciated that photomask 28 and image 60 appear in the same location at subject plane 30 during, respectively, the exposure and reconstruction of the hologram. Light rays 32 diffracted by photomask 28 travel along the same path as but in a direction opposite to light rays 32' that carry the defect image pattern.

Figure 3A:
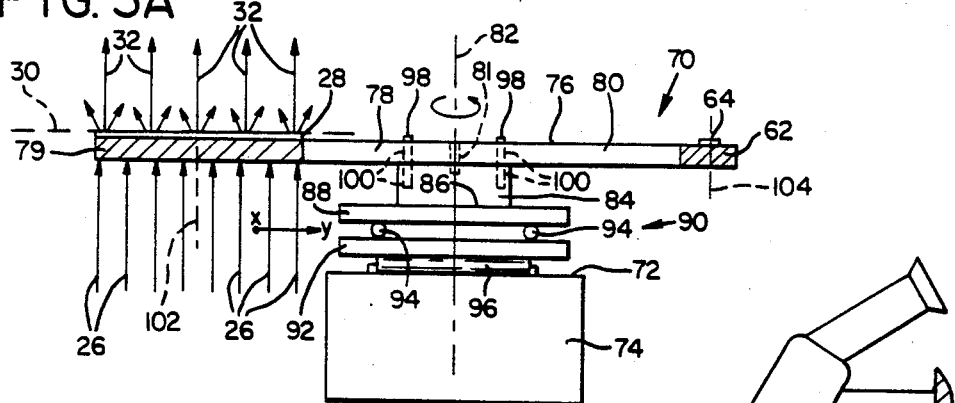
FIGS. 3A and 3B are enlarged side elevation views of the rotatable and translatable mounting mechanism of the present invention in, respectively, the exposure orientation and the inspection orientation.
Figure 3B:
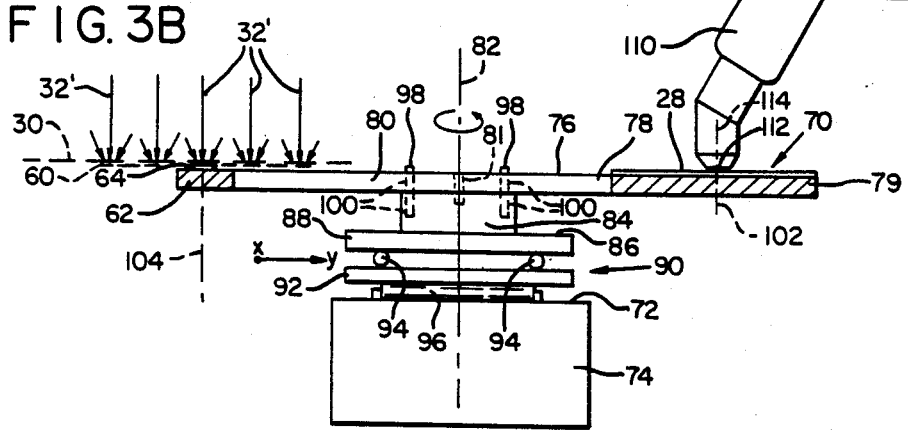
Figure 4:
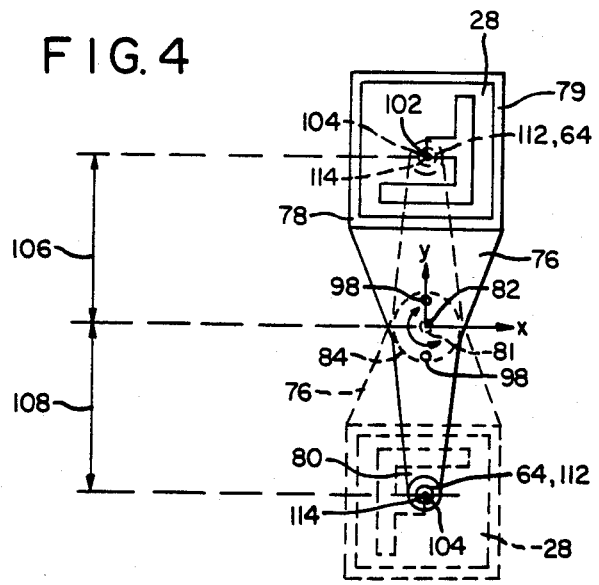
FIG. 4 is a plan view of the plate of the mounting mechanism which is shown in solid lines for the exposure orientation of FIG. 3A and in phantom lines for the inspection orientation of FIG. 3B.

FIGS. 3A and 3B and FIG. 4 show the rotatable and translatable mounting mechanism 70 of the present invention onto which photomask 28 can be mounted for both exposing hologram 42 and inspecting image 60. One of the advantages of mounting mechanism 70 is that the inspection of a region of image 60 can be coordinated with an examination of the corresponding region of photomask 28 as will be described below. FIG. 3A shows mounting mechanism 70 in an orientation for exposing photomask 28 to parallel coherent light rays 26 from beam expander 24. FIG. 3B shows mounting mechanism 70 in an orientation for inspecting image 60 by video camera 62.

With reference to FIGS. 3A and 3B, mounting mechanism 70 is supported on the horizontal surface 72 of a rigid table 74, which is preferably constructed with stainless steel horizontal and vertical members (not shown) for structural rigidity and with a thin wall honeycomb inner-core for structural lightness. The laser 10, beam splitter 16, beam expanders 24 and 50, and mirrors 14, 22, 46, 48, 54, and 56, all of which are depicted in FIG. 1, are preferably positioned below horizontal surface 72. The remaining optical components shown in FIGS. 1 and 2 are preferably positioned above horizontal surface 72 of table 74.

Mounting mechanism 70 comprises a plate 76 that includes a substrate arm 78 and a camera arm 80 which are arranged 180° apart in a plane parallel to horizontal subject plane 30. Arm 78 has a transparent holder 79 which carries photomask 28 by its edges; arm 80 carries video camera 62. Plate 76 is secured to a shaft 81 that is journalled for rotation about a vertical axis 82 in a pedestal 84 which is rigidly supported on the upper surface 86 of the Y direction stage 88 of a linear positioning table assembly 90.

Linear positioning table 90 comprises Y stage 88 and an X direction stage 92 which are mounted on bearing assemblies 94 and 96, respectively, and stacked so that plate 76 can travel to various X-Y position coordinate combinations. Linear positioning table assembly 90 is a commercially available system, such as a Model 8500 positioning table manufactured by Kensington Laboratories, Inc. of Richmond, Calif. Positioning table assembly 90 of the preferred embodiment has a 10.8 inch travel in the X direction and a 6.9 inch travel in the Y direction. The positions of Y stage 88 and X stage 92 can be moved independently of each other by DC servo motors (not shown) or by manual drive controls.

FIG. 4 shows plate 76 in solid lines in the exposure orientation and in phantom lines in the inspection orientation. An "F" is used as an exemplary pattern for photomask 28 for purposes of illustration only.

With reference to FIG. 4, plate 76 is rotatable about axis 82 and can be locked into either the exposure position or the inspection position by removable pins 98 that fit through axially aligned bores 100 in plate 76 and pedestal 84 (FIGS. 3A and 3B). The centers of bores 100 are collinear with axis of rotation 82. The exposure and inspection orientations of plate 76 are achieved by rotating it 180° about axis of rotation 82. Such rotation is preferably accomplished manually but can also be accomplished by a motor-driven mechanism. Precision machining of pins 98 and bores 100 in plate 76 and pedestal 84 ensures that a precise 180° rotation is accomplished.

Photomask 28, which has a center point 102, and video camera 62, which has a field of view center point 104, are mounted on plate 76 so that the center points 102 and 104 are collinear with and equidistant from axis of rotation 82. The distance 106 from axis 82 and center 102 and the distance 108 from axis 82 and center 104 are each about 20 cm.

With reference to FIGS. 3A and 4, whenever photomask 28 is exposed to produce hologram 42, plate 76 is rotated into position so that photomask 28 receives the parallel coherent light rays 26 exiting beam expander 24. As shown in FIG. 3A, light rays 26 propagate upwardly and strike photomask 28. The diffracted light rays 32 propagate toward and strike the photosensitive medium to record hologram 42. Video camera 62 is disabled while plate 76 is in its exposure orientation.

With reference to FIGS. 3B and 4, whenever image 60 is inspected to determine, for example, the presence of defects in photomask 28, plate 76 is rotated 180° relative to its exposure orientation into position so that video camera 62 receives the defect image that is carried by the light rays developed from hologram 42. As shown in FIG. 3B, light rays 32' propagate downwardly and intersect horizontal subject plane 30 to form image 60. A viewing means 110, such as a microscope, which is supported separate from plate 76, is used to inspect photomask specimen pattern 28 as video camera 62 detects image 60.

With reference to FIGS. 3A and 3B and FIG. 4, whenever the center 102 of photomask 28 and field of view center 104 of video camera 62 are equidistant from and collinear with axis of rotation 82, the operations of video camera 62 and microscope 110 can be coordinated so that the region of image 60 in the field of view 64 of video camera 62 can correspond to the region of photomask 28 in the field of view 112 of stationary microscope 110. This is accomplished by aligning the field of view center 104 of video camera 62 and the field of view center 114 of microscope 110 with axis of rotation 82. Video camera 62 scans the image 60 by moving linear positioning table assembly 90 in pure translation. Such translational movement synchronously positions photomask 28 under microscope 110 so that video camera 62 and microscope 110 automatically track and observe corresponding regions of image 60 and photomask 28, respectively. The region in the field of view 112 of microscope 110 has, therefore, position coordinates that are in one-to-one correspondence to the position coordinates of the region of image 60 in the field of view 64 of video camera 62.

It will be appreciated that under the above-described conditions and in the absence of spatial filter 69 from the apparatus, the "F" pattern appears in the same location at subject plane 30 as either photomask 28 in the exposure orientation or image 60 in the inspection orientation. FIG. 4 shows the alignment and the overlap of the fields of view of video camera 62 and microscope 110 relative to the "F" pattern, with field of view 64 of video camera 62 being superimposed on arm 78 in the exposure orientation and field of view 112 of microscope 110 being superimposed on arm 80 in the inspection orientation.

To accomplish the synchronous tracking of corresponding regions of photomask 28 and image 60, it is, therefore, necessary that (1) the rotation angle between the exposure and inspection orientations be exactly 180°, (2) the center lines between the fields of view of video camera 60 and microscope 110 be collinear, and (3) the distances 106 and 108 be equal. If distances 106 and 108 are not equal (i.e., the axis of rotation 82 is off center), the fields of view of photomask 28 and image 60 can be brought into alignment by performing a Y axis translation of plate 76 after it is rotated into the inspection orientation. The amount of translation required is equal to one-half the difference between the distances 106 and 108 and is performed in the direction opposite to that of the offset of axis 82.

It will be appreciated that a typical photomask 28 comprises not a single "F" pattern but a plurality of normally identical elements that are mutually spaced apart in a regular two-dimensional array. Whenever plate 76 is in the inspection orientation and spatial filter 69 is positioned in filter plane 38, only the defects in a photomask 28 of the type described appear as image 60 in the positions corresponding to their locations in the photomask.

It will be obvious to those having skill in the art that many changes may be made in the above-described details of the preferred embodiment of the present invention. For example, the mounting mechanism can be used during a semiconductor printing process for checking the registration of a mask against the reconstructed image of previously printed layers of a semiconductor wafer before the mask pattern is printed onto the wafer. The scope of the present invention, therefore, should be determined only by the following claims.

What is claimed is:

1. In an optical processing apparatus having recording means for making a recording of light information that corresponds to a specimen pattern and light pattern forming means for forming from the recording a light pattern that corresponds to the speciment pattern, a rotatable and translatable mechanism for mounting the specimen pattern and scanning the light pattern, comprising:
    a plate for supporting the speciment pattern;
    detecting means operatively connected to the plate for detectring the light pattern;
    translating means for providing translational movement of the plate in a plane; and
    rotating means for rotating the plate about an axis that intersects the plate, the rotating means selectively rotating the plate to a first position so that the recording means is operable to make the recording of light information and to a second position so that the translating means is operable to move the plate in the plane and enable the detecting means to scan and detect the light pattern.

2. The apparatus of claim 1 in which the light pattern is formed in the location occupied by the specimen pattern in the first position.

3. The apparatus of claim 1 in which the plate has a surface, and the axis of rotation is substantially perpendicular to the surface.

4. The apparatus of claim 1 in which the plate has a surface, and the specimen pattern and detecting means are supported on the surface on opposite sides of the axis of rotation.

5. The apparatus of claim 4 in which both the specimen pattern and the light pattern have position coordinates that represent the location of a corresponding region in the specimen pattern and the light pattern; and wherein the apparatus further comprises a viewing means for viewing a region of the specimen pattern, the viewing means being supported separate from the plate and positioned relative to the detecting means so that the region in the view of the viewing means has position coordinates that are in one-to-one correspondence to the position coordinates of the region of the light pattern detected by the detecting means.

6. The apparatus of claim 1 wherein the apparatus further comprises a viewing means that is supported separate from the plate for viewing a region of the specimen pattern.

7. The apparatus of claim 6 in which the detecting means has a first field of view with a first center and a second field of view with a second center, the first and second centers and the axis of rotation being aligned so that they are collinear.

8. The apparatus of claim 7 in which the distance between the first center and the axis of rotation and the distance between the second center and the axis of rotation are equal, and the first and second positions are separated by an angle of 180°.

9. The apparatus of claim 7 in which the translating means is operable to reposition the axis of rotation in a direction such that the distance between the first center and the axis of rotation and the distance between the second center and the axis of rotation can be made equal.

10. In an optical processing apparatus having recording means for making a recording of light information that corresponds to a specimen pattern and light pattern forming means for forming from the recording a light pattern that corresponds to defects present in the specimen pattern, a rotatable and translatable mechanism for mounting the specimen pattern and scanning the light pattern, comprising:

a plate for supporting the specimen pattern;

detecting means operatively connected to the plate for detecting the light pattern;

translating means for providing translational movement of the plate in a plane; and rotating means for rotating the plate about an axis that intersects the plate, the rotating means selectively rotating the plate to a first position so that the recording means is operable to make the recording of light information and to a second position so that the translating means is operable to move the plate in the plane and enable the detecting means to scan and detect the light pattern.

* * * * *